United States Patent [19] [11] 4,353,893
Watanabe et al. [45] Oct. 12, 1982

[54] KA-6606 AMINOGLYCOSIDES ANTIBIOTICS AND COMPOSITIONS THEREOF

[75] Inventors: Isamu Watanabe, Higashimurayama; Takashi Yamaguchi, Seki; Kazuhiro Kamiya; Toshihito Mori, both of Higashimurayama, all of Japan

[73] Assignee: Kowa Company, Ltd., Aichi, Japan

[21] Appl. No.: 265,562

[22] Filed: May 20, 1981

[30] Foreign Application Priority Data

May 22, 1980 [JP] Japan ................................. 55-67084
Jun. 17, 1980 [JP] Japan ................................. 55-80842

[51] Int. Cl.$^3$ ...................... A61K 31/71; C07H 15/22
[52] U.S. Cl. .................... 424/180; 536/17 R
[58] Field of Search .................. 536/17 R, 17 B; 424/180

[56] References Cited

U.S. PATENT DOCUMENTS 4,001,208  1/1977  Umezawa et al. ............... 536/17 R
4,214,080  7/1980  Carney ............................. 536/17 R
4,242,503 12/1980 Lartey et al. .................... 536/17 R
4,312,858  1/1982  Deushi et al. .................... 536/17 R Primary Examiner—Johnnie R. Brown
Attorney, Agent, or Firm—Wenderoth, Lind & Ponack

[57] ABSTRACT

A compound of the general formula:

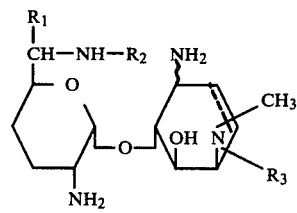

wherein $R_1$ and $R_2$ are different and each represents a hydrogen atom or a methyl group, $R_3$ represents a hydrogen atom, or a glycyl group which may be substituted, and the symbol === between the carbon atoms at the 5- and 6- positions represents a single or double bond, and an acid addition salt thereof; and its antibiotic use.

3 Claims, No Drawings

KA-6606 AMINOGLYCOSIDES ANTIBIOTICS AND COMPOSITIONS THEREOF

This invention relates to novel aminoglycosides useful as antibiotics, and an antibiotic use thereof.

More specifically, this invention relates to compounds of the following formula:

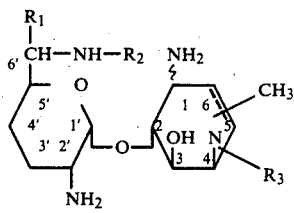
(I)

wherein $R_1$ and $R_2$ are different and each represents a hydrogen atom or a methyl group, $R_3$ represents a hydrogen atom, or a glycyl group which may be substituted, and the symbol between the carbon atoms and at the 5- and 6- positions represents a single or double bond, and acid addition salts thereof.

This invention also pertains to an antibiotic comprising the compound of formula (I) or its pharmaceutically acceptable acid addition salt as an active ingredient.

Some of the inventors of the present application and others already proposed aminoglycosides including compounds of the following formula (A), a process for production thereof and an antibiotic use thereof (West German OLS No. 2813021 published Oct. 5, 1978; Japanese Laid-Open Patent Publication No. 111497/1980 published on Aug. 28, 1980; West German OSL No. 2928373 published on Jan. 24, 1980; and West German OLS No. 2942194 published on Apr. 24, 1980).

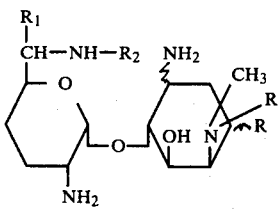
(A)

wherein $R_1$ and $R_2$ are as defined above with regard to formula (I), R represents a member selected from the class consisting of a hydrogen atom and an optionally substituted glycyl group such as $—COCH_2NH_2$, $—COCH_2NHCONH_2$ or $—COCH_2NHCHO$, and $R_4$ represents $—OH$ or $—OCH_3$.

The present inventors have made extensive investigations about the development of derivatives of the above-exemplified known aminoglycosides. These investigations have led to the discovery that the novel aminoglycosides of formula (I) and acid addition salts thereof can be produced easily in good yields, and that the compounds of formula (I), i.e. 5-demethoxy-KA-6606 or -KA-7038 compounds which do not have a methoxy or hydroxyl group at the 5-position and the acid addition salts thereof exhibit increased antibiotic ability.

It is an object of this invention to provide novel compounds useful as antibiotics, and an antibiotic use thereof.

The above and other objects and advantages of this invention will become more apparent from the following description.

The starting aminoglycoside used to produce the compound of formula (I) is expressed by the following formula:

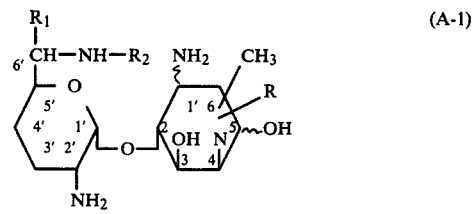
(A-1)

wherein R, $R_1$ and $R_2$ are as defined above with regard to formula (A).

The compounds of formula (A-1) [5-de-O-methyl-KA6606 compounds and 5-de-O-methyl-KA7038 compounds] can be produced from KA6606 compounds and KA7038 compounds of the following formula:

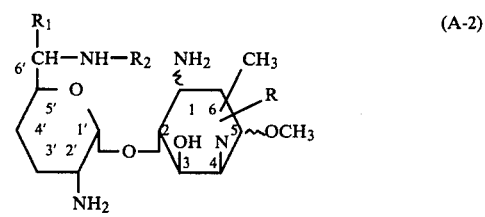
(A-2)

wherein R, $R_1$ and $R_2$ are as defined hereinabove with regard to formula (A).

The production of the compounds of formula (A-1) from the compounds of formula (A-2) and the production of the compounds (A-2) are described in detail, for example, in the above-cited West German OLS No. 2942194, 2813021 and 2928373.

As described in detail in West German OLS No. 2942194, the compounds of formula (A-1) which can be used in the production of the compounds (I) can be produced by treating KA-6606 compounds such as KA-6606 I, KA-6606 II, KA-6606 III, KA-6606 IV, KA-6606 VI and KA-6606 VIII, and KA-7038 compounds such as KA-7038 I, KA-7038 III and KA-7038 VI, which can be represented by formula (A-2), with strong acids.

The above treatment induces the cleavage of the methyl ether at the 5-position of the compounds (A-2) (de-O-methylation) to give compounds of formula (A-1) in which the 5-position is substituted by OH. When a compound of formula (A-1) in which R is a hydrogen atom is obtained as a result of this treatment, the amino or methylamino groups at the 1-, 2'- and 6'-positions of the compound are protected and then the compound is acylated with an optionally substituted amino acid such as glycine or a reactive derivative thereof, followed by splitting off the protective group. Consequently, a compound of formula (A-1) having the desired R can be obtained. If desired, the compounds (A-1) may be converted to their acid addition salts by contact with suitable acids.

Examples of the strong acid are strong mineral acids such as hydrobromic acid, hydrochloric acid, hydriodic acid, hydrofluoric acid, sulfuric acid and phosphoric acid; strongly acidic organic acids such as p-toluenesulfonic acid and trifluoromethanesulfonic acid; and Lewis acids such as boron trichloride and boron trifluoride. When a Lewis acid is used, the reaction is preferably carried out in an anhydrous condition. For example, dichloromethane can be used as an anhydrous solvent. In other cases, the reaction is preferably carried out in aqueous solution.

The reaction can be carried out, for example, at room temperature to about 200° C. Usually, the reaction ends in about 1 hour to about 30 days. The product can be separated and purified by an ordinary column chromatographic method, for example by using a cation exchange resin.

The protective group used in the above reaction may be any of known groups used in peptide synthesis, such as benzyloxycarbonyl, butoxycarbonyl, and benzoylisopropenyl.

The novel aminoglycosides of formula (I) in accordance with this invention can be produced easily in good yields from the known compounds of formula (A-1) which can be produced by the method disclosed in detail in West German OLS No. 2942194. Specifically, replacement of the —OH group at the 5-position of the compounds of formula (A-1) by H gives the compounds of formula (I). Various methods can be employed in the reaction of forming the deoxy compound. For examples, the following methods (A) to (I) may be cited.

(A) The hydroxyl group at the 5-position is sulfamoylated (e.g., N,N-dimethylsulfamoylated), or sulfonylated (e.g., trifluoromethanesulfonylated). The product is reacted with metallic sodium in liquid ammonia to cleave the carbon-oxygen bond at the 5-position [T. Tsuchiya, I. Watanabe, S. Umezawa et al: Tetrahedron Letters, 3365 (1978)].

(B) The hydroxyl group at the 5-position is substituted by a halogen atom to give a 5-halo(preferably 5-chloro) compound, which is then dehalogenated by the action of tri-n-butyl stannane [H. Arita, N. Ueda and Y. Matsushima: Bull. Chem. Soc. Jpn. 45, 567 (1972)].

(C) The hydroxyl group at the 5-position is esterified with phosphoric acid, preferably substituted phosphoric acid such as bis-dimethylaminophosphoric acid, and then reduced with lithium in the presence of, for example, ethylamine [S. Oida, H. Saeki, Y. Ohashi and E. Ohki: Chem. Pharm. Bull. 23, 1547 (1975)].

(D) The hydroxyl group at the 5-position is oxidized to a carbonyl group, and then converted to a hydrazone such as tosylhydrazone, and then reduced with sodium cyanoborohydride, for example [Vasu Nair and A. K. Sinhababu: J. Org. Chem. 43, 5013 (1978)].

(E) Thiobenzoate or S-methyldithiocarbonate is formed at the 5-position, and then reacted with tri-n-butyl stannane [Derek H. R. Barton and Raman Subramanian: J. Chem. Soc. Perkin trans I, 1977, 1718].

(F) A sulfonate ester is formed at the 5-position and then halogenated (preferably, iodinated), followed by catalytic reduction [D. Ikeda, T. Tsuchiya, S. Umezawa and H. Umezawa: J. Antibiot., 26, 799 (1973)].

(G) The compound is trifluoromethanesulfonylated at the 5-position, and then photolyzed [T. Tsuchiya, F. Nakamura and S. Umezawa: Tetrahedron Letters 2805 (1979)].

(H) A sulfonate ester is formed at the 5-position and a neutral, acidic or basic salt is caused to act on it to induce elimination reaction and thus provide unsaturation [H. R. Bollinger and D. A. Prins: Helv. Chim. Acta 29, 1061 (1946)].

(I) An S-methyldithiocarbamate is formed at the 5-position, and then thermally decomposed to provide unsaturation [R. J. Ferrier: J. Chem. Soc. 1964, 5443].

The unsaturated compounds obtained by methods (H) and (I) may, if desired, be reduced to saturated compounds. The reduction may be carried out by a catalytic reducing method using platinum, palladium or nickel as a catalyst. The reaction can be performed at 0° to 100° C. under atmospheric or elevated pressures.

As the starting compounds of formula (A-1) used in the production of the compounds of the invention represented by formula (I), the following known compounds (5-de-O-methyl-KA6606 and 5-de-O-methyl-KA-7038 compounds) can be exemplified.

5-de-O—methyl-KA6606 I:-

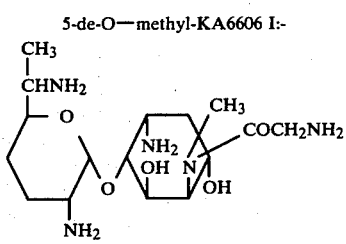

5-de-O—methyl-KA6606 II:-

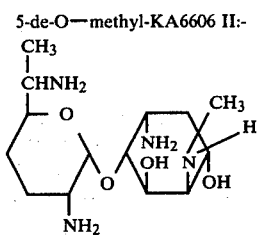

5-de-O—methyl-KA6606 III:-

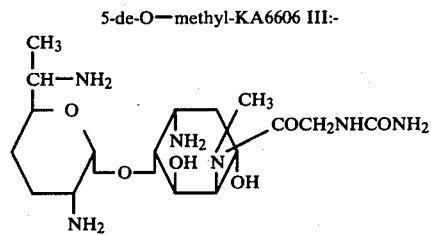

5-de-O—methyl-KA6606 IV:-

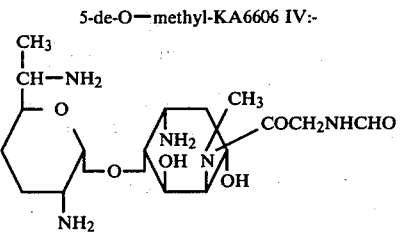

5-de-O—methyl-KA6606 VI:-

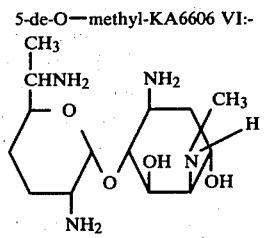

5-de-O—methyl-KA6606 VIII:-

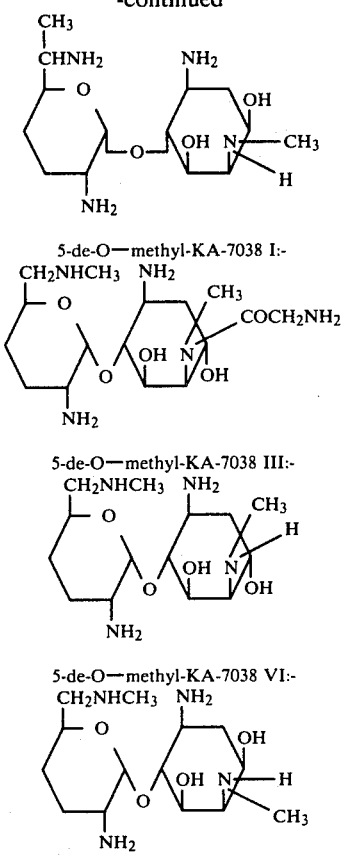

The novel aminoglycosides of formula (I) in accordance with this invention can be produced by subjecting the above-exemplified known aminoglycosides of formula (A-1) to deoxygenation reaction at the 5-position by the methods (A) to (I) described above.

Preferably, each of amino groups and the hydroxyl group at the 3-position are protected before performing the reactions in accordance with the methods (A) to (I) for replacement of the hydroxyl group at the 5-position by H.

Known protective groups for amino which are conventionally used in peptide synthesis can be used. Preferred protective groups are those of the following general formula:

wherein A represents an alkyl group preferably having 1 to 6 carbon atoms, a cycloalkyl group preferably having 5 to 8 carbon atoms, an aryl group preferably having 6 to 10 carbon atoms, or an aralkyl group preferably consisting of a $C_1$-$C_6$ alkyl group and $C_6$-$C_{10}$ aryl group; and a $\beta$-dicarbonyl group. Specific examples of the protective groups include alkyloxycarbonyl groups such as ethyloxycarbonyl, tert-butyloxycarbonyl or tert-amyloxycarbonyl, cycloalkyloxycarbonyl groups such as cyclohexyloxycarbonyl, aryloxycarbonyl groups such as phenoxycarbonyl, and aralkyloxycarbonyl groups such as benzyloxycarbonyl, p-methoxybenzyloxycarbonyl or benzylisopropenyl.

Introduction of the protective groups may be effected by conventional methods known in the art. Preferably, it is preformed by the action of a carboxylic acid of the general formula:

 (II)

wherein A is as defined hereinabove, or its reactive derivative on the compound of formula (A-1). Examples of the reactive derivatives of the carboxylic acid are acid halides, acid azide compounds, acid anhydrides and active esters. When using the acid halides, the reaction can be performed in the same way as in the usual Shotten-Baumann reaction. When using the acid anhydrides or active esters, the reaction can be performed by the action of 1 to 10 equivalents, per equivalent of the compound of formula (A-1), of these reactive derivatives in a solvent such as methanol at a temperature of about $-10°$ C. to about $100°$ C.

Thereafter, only the hydroxyl group at the 3-position is selectively protected. Since a methyl amino group is present at the 4-position adjacent the hydroxyl group at the 3-position in the compound of formula (A-1), it is also possible to protect the hydroxyl group at the 3-position and the methylamino group at the 4-position together easily by forming a cyclic carbamate. The cyclic carbamate can be formed by the action of an alkali, preferably in a solvent, on the tetra-N-protected product of the compound of formula (A-1). Examples of the alkali are sodium hydride, barium hydroxide, sodium hydroxide and calcium hydroxide. The solvent may, for example, by dimethyl formamide, dioxane, tetrahydrofuran, water, or mixtures thereof. The reaction may be carried out, for example, at a temperature of about $-20°$ C. to about $100°$ C. for about 0.1 to about 10 hours. The amount of the alkali is, for example, about 0.01 to about 10 equivalents.

In the process of this invention, a compound of formula (I) in which $R_3$ is a hydrogen atom, i.e. the 4-position is a methylamino group, can be converted to another compound of formula (I) in which the 4-position is a glycyl group which may be substituted. For this conversion, first the methylamino group at the 4-position is converted to a free amino group which is then acylated. For example, by hydrolyzing the cyclic carbamate between the 3- and 4-positions, the methylamino group at the 4-position can be easily converted to a free amino group. Hydrolysis can be performed in a customary manner in under acidic or alkaline conditions. The reaction can be performed, for example, at a temperature of 30° to 100° C. for about 0.1 to about 50 hours in an aqueous medium. Examples of acids and alkalies used include sulfuric acid, hydrochloric acid, sodium hydroxide, potassium hydroxide and barium hydroxide.

When the compound of formula (I) having a methylamino group at the 4-position used in the above conversion reaction is the one in which the protective groups introduced prior to the deoxygenation reaction of the compound of formula (A-1) have been split off, the amino groups in the 1-, 2'- and 6'-positions of such compound of formula (I) are again protected prior to performing the conversion reaction. This protection of the amino groups can be performed in the same way as in the protection of the amino groups in the compound of formula (A-1). Since at this time, the methylamino group at the 4-position is simultaneously protected, it is necessary to convert the methylamino group at the 4-position to be acylated to a free amino group. The methylamino group at the 4-position alone can be easily converted to a free amino group by forming a cyclic carbamate between the hydroxyl group at the 3-position and the methylamino group at the 4-position, and then hydrolyzing the cyclic carbamate in the manner described hereinabove.

Alternatively, the methylamino group at the 4-position may be directly converted to a free amino group by causing an alkali such as barium hydroxide to act on the tetra-N-protected product of the compound of formula (I) in a solvent, such as dioxane or tetrahydrofuran, containing water at a temperature of about −10° C. to about 100° C.

When, in the protection of the amino groups of the compound of formula (A-1) in which R is hydrogen or the compound of formula (I) in which $R_3$ is hydrogen, an active ester such as a substituted phenyl ester, N-hydroxysuccinimide ester or N-hydroxyphthalimide ester, particularly an active ester of the following general formula:

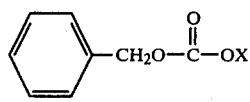

wherein X represents an optionally substituted phenyl group, succinimidyl group or phthalimidyl group, is used as the reactive derivative of the carboxylic acid of formula (II), the amino groups at the 1-, 2'- and 6'-positions can be selectively protected. Better results can be obtained in this reaction if it is carried out in the presence of a metallic compound such as nickel acetate, cobalt acetate and copper acetate.

Acylation of the methylamino group at the 4-position of the compound of formula (I) in which $R_3$ is hydrogen and the amino groups at the 1-, 2'- and 6'-positions are protected gives a compound of formula (I) in which $R_3$ is glycyl and the the amino groups are protected.

Preferred acylating agents are amino acids such as glycine. Acylation with amino acids can be performed in accordance with usual peptide synthesizing methods by the action of N-protected amino acids or the reactive derivatives thereof. Any of the aforesaid protective groups can be used to protect the amino group of the amino acids. The protective group for the amino acids may be the same or different as or from the protective groups in the compound of formula (I) in which $R_3$ is hydrogen. Preferably, it is the same protective group in order to perform the deblocking reaction in the subsequent step easily. The reactive derivatives of the amino acids may be the same as the reactive derivatives of the carboxylic acid of formula (II).

A compound of formula (I) having no protective group is obtained by splitting off the protective groups of the compound of formula (I) in which $R_3$ is hydrogen or a glycyl group and the amino groups and/or hydroxyl groups are protected. Elimination of the protective groups for the amino groups and hydroxyl groups can be effected by usual methods. Preferably by catalytic reduction or acid hydrolysis. For example, palladium, platinum, Raney nickel, rhodium, and nickel can be used as a catalyst for catalytic reduction. Solvents that can be used in the deprotection reaction include water, methanol, ethanol, dioxane, tetrahydrofuran, acetic acid, and mixtures thereof. The catalytic reduction can be performed, for example, under a hydrogen pressure of about 1 to about 5 atmospheres at a temperature of about 0° to about 100° C. for about 0.1 to about 10 hours.

According to still another embodiment, a compound of formula (I) in which $R_3$ is a glycyl group —COCH$_2$NH$_2$ can be converted to a compound of formula (I) in which $R_3$ is a substituted glycyl group such as —COCH$_2$NHR'' by, for example, formimidoylating or amidinating the glycyl group. R'' in the above formula is preferably —CH=NH or

The formimidoylation can be carried out, for example, by reacting the compound of formula (I) in which $R_3$ is a glycyl group with formimide acid or its reactive derivative in the presence of a base in a solvent. Examples of the base used include alkali metals such as metallic lithium, metallic sodium and metallic potassium; alkali hydrides such as lithium hydride, sodium hydride and potassium hydride; and alkali alkoxides such as lithium methoxide, lithium ethoxide, sodium methoxide, sodium ethoxide, potassium methoxide and potassium ethoxide. The solvent may include, for example, alcohols such as methanol, ethanol, n-propanol and isopropanol, hydrocarbons such as benzene, toluene, xylene, cyclohexane, petroleum ether and petroleum benzin, and ethers such as diethyl ether, methyl ethyl ether, dioxane and tetrahydrofuran. The reactive derivative of formimide acid may include, for example, esters, anhydrides and halides of formimide acid.

The formimidoylation reaction can be performed in a solvent of the types exemplified hereinabove in the presence of a base of the types exemplified hereinabove at a temperature of about 0° to about 80° C. for about 1 to about 30 hours.

The amidination may be carried out by reacting the compound of formula (I) in which $R_3$ is a glycyl group with guanylpyrazole having the primary amino group protected (the pyrazole ring may be substituted by an alkyl group, an alkoxy group, etc.) and then eliminating the protective group. Nitro and benzyloxycarbonyl groups may be cited as examples of the protective group for the guanidino group. The reaction can be performed in the same solvent as used in the aforesaid formimidoylation. The reaction proceeds at room temperature, but may be promoted by heating. Heating can be done, for example, to a temperature of about 70° C. Elimination of the protective group is performed in a customary manner, but catalytic reduction is preferred.

According to another embodiment, the above amidination can be performed by reacting the compound of formula (I) in which $R_3$ is a glycyl group with cyanamide. This reaction can be performed at a temperature of from room temperature to about 150° C. in the presence of an acid such as hydrochloric acid or hydrobromic acid.

According to still another embodiment, the amidination may be carried out by reacting the compound of formula (I) in which $R_3$ is a glycyl group with an S- or O-methylisourea, such as S-methylisothiourea or O-methylisourea, or a salt thereof. The reaction can be carried out, for example, at a temperature of about 0° to about 40° C. for about 1 to about 24 hours in a solvent such as dimethyl sulfoxide, dimethyl formamide and hexamethyl phosphoramide.

In the formimidoylation reaction or the amidination reaction described above, the compound of formula (I) in which $R_3$ is a glycyl group is preferably in a form in which the amino groups at the 1-, 2'- and 6'-positions are protected and only the amino group of the glycyl group at the 4-position is free.

Introduction of such a protective group can be performed in the same way as described above with regard to the introduction of protective groups preferably effected prior to the 5-deoxygenation reaction of the starting compound of formula (A-1).

For example, the amino groups at the 1-, 2'- and 6'-positions can be selectively protected by using active esters of the carboxylic acid described hereinabove, preferably a substituted phenyl ester, N-hydroxysuccinimide ester or N-hydroxyphthalimide ester. Furthermore, when the methylamino group at the 4-position is simultaneously protected as mentioned hereinabove, the methylamino group at the 4-position alone can be selectively converted to a free amino group by forming a cyclic carbamate between the hydroxyl group at the 3-position and the methylamino group at the 4-position and then hydrolyzing the cyclic carbamate. Or the methylamino group at the 4-position can be directly converted to a free amino group by the action of an alkali on the tetra-N-protected compound of formula (I) in a solvent containing water, as described hereinabove.

Various acylating agents as exemplified above can be used to convert the methylamino group at the 4-position to a glycyl group. Preferred acylating agents are active derivatives at the carboxyl group of glycine having the amino group protected. Preferred as the protective group for the amino group of glycine is a protective group which does not induce elimination of other protective groups (preferably benzyloxycarbonyl) when it is to be eliminated. Examples of the preferred protective group are diphenylphosphinothioyl, tert.butoxycarbonyl, and p-methoxybenzyloxycarbonyl. When, subsequent to acylation, the protective group for the glycyl group is eliminated, for example by acid treatment, a 1,2',6'-tris-N-protected product of the compound of formula (I) in which $R_3$ is a glycyl group is obtained.

Elimination of the amino protective group of the compound of formula (I) which is formimidoylated or amidinated can be split off by usual methods. Preferably, a catalytic reducing method is used.

In the present invention, the compound of formula (I) that can be obtained from the compound of formula (A-1) in the above manner can be isolated and purified in a customary manner. Column chromatography is preferred. Preferred adsorbents for this purpose are cation exchange resins such as CM-Sephadex, Amberlite IRC-50, Amberlite IRC-84, Amberlite CG-50, and carboxymethyl cellulose. Development can be performed by a gradient method or a stepwise method using an alkaline aqueous solution such as an aqueous solution of ammonia or an aqueous solution of ammonium formate as a developing solvent. The active fractions are collected from the eluates, and lyophilized to obtain the compound of formula (I) in pure form.

Depending upon the purifying operation, the desired product (I) may also be obtained in the form of an acid addition salt. The compound (I) as a free base can be converted to an acid addition salt thereof, preferably a pharmaceutically acceptable acid addition salt thereof, in a customary manner. Acids for this purpose include, for example, inorganic acids such as sulfuric acid, hydrochloric acid, hydrobromic acid, hydriodic acid, phosphoric acid, carbonic acid and nitric acid, and organic acids such as acetic acid, fumaric acid, malic acid, citric acid, mandelic acid and succinic acid.

The novel aminoglycosides of formula (I) exhibit superior antibiotic activity, and are useful in the field of medicines for man and animals, and also as intermediates for the synthesis of derivatives.

Accordingly, the present invention also provides an antibiotic composition composed of an antibiotically effective amount of a compound of the formula:

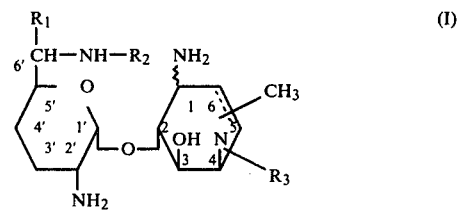

wherein $R_1$ and $R_2$ are different and each represents a hydrogen atom or a methyl group, $R_3$ represents a hydrogen atom, or a glycyl group which may be substituted, and the symbol ⸺ between the carbon atoms at the 5- and 6-positions represents a single or double bond, or a pharmaceutically acceptable acid addition salt thereof, and a pharmaceutically acceptable diluent or carrier.

The amount of the compound (I) is, for example, about 0.01 to about 99.5% by weight, based on the weight of the composition.

The antibiotic composition of this invention may be in any dosage forms usually employed, but injecting preparations and capsules are especially preferred.

Preferably, like known water-soluble basic antibiotics, an injectable is prepared by filling a lyophilized powder of the antibiotic into a vial, preferably together with a stabilizer, and in use, the contents of the vial are dissolved in a dissolving liquid for administration.

The diluent or carrier includes, for example, liquid diluents such as distilled water for injection and physiological isotonic solution, and solid carriers such as lactose, starch, white sugar, glucose, crystalline cellulose, calcium carbonate, kaolin, D-mannitol, magnesium metasilicate aluminate, calcium sulfate, calcium phosphate and bentonite. Addition of stabilizers such as acidic sodium bisulfite is also preferred.

The dosage of the antibiotic substance of this invention can be suitably selected, and is, for example, about 0.01 to about 100 mg/kg/day.

Thus, according to this invention, there can be provided antibiotic compositions for animals other than human, such as poultry domesticated animals and cultivated fish, and antibiotic compositions for human beings. These compositions are useful as antibacterial agents having a broad antibacterial spectrum.

The antibacterial spectra of 5-demethoxy-KA-6606 I (A), 4-N-glycyl-5-demethoxy-KA-6606 VI (B) and 5-demethoxy-KA-7038 I (C) as typical examples of the novel compounds of formula (I) are shown in Table 1 in comparison with those of KA-6606 I (A'), 4-N-glycyl-KA-6606 VI (B') and KA-7038 I (C') having a methoxy group at the 5-position.

TABLE 1

| Test bacteria | Minimum inhibition concentration (mcg/ml) | | | | | |
|---|---|---|---|---|---|---|
| | A | A' (Comparison) | B | B' (Comparison) | C | C' (Comparison) |
| Staphylococcus aureus 209P | 0.2 | 0.39 | 0.39 | 0.78 | 0.39 | 0.78 |
| Bacillus subtilis ATCC 6633 | ≦0.1 | 0.2 | ≦0.1 | 0.2 | ≦0.1 | 0.2 |
| Streptococcus faecalis | 12.5 | 25 | 12.5 | 25 | 25 | 50 |
| Escherichia coli NIHJ | 1.56 | 1.56 | 1.56 | 1.56 | 3.13 | 3.13 |
| Escherichia coli K-12 ML1410 | 1.56 | 3.13 | 3.13 | 6.25 | 1.56 | 3.13 |
| Escherichia coli K-12 ML1410 R-81 (*1) | 1.56 | 3.13 | 3.13 | 6.25 | 3.13 | 6.25 |
| Escherichia coli K-12 ML1410 R-101 (*2) | 1.56 | 3.13 | 3.13 | 6.25 | 6.25 | 12.5 |
| Escherichia coli 176 (*3) | 0.78 | 1.56 | 1.56 | 3.13 | 3.13 | 6.25 |
| Proteus vulgaris OX-19 | 1.56 | 1.56 | 1.56 | 1.56 | 3.13 | 3.13 |
| Klebsiela pneumoniae PCI602 | 0.78 | 1.56 | 0.78 | 1.56 | 1.56 | 3.13 |
| Pseudomonas aeruginosa Shibata | 1.56 | 6.25 | 3.13 | 12.5 | 3.13 | 12.5 |
| Pseudomonas aerginosa GN315 (*4) | 3.13 | 12.5 | 3.13 | 12.5 | 6.25 | 25 |
| Proteus inconstans (*5) | 6.25 | 6.25 | 6.25 | 6.25 | 6.25 | 6.25 |
| Serratia marcescens | 0.78 | 1.56 | 0.78 | 0.78 | 0.78 | 1.56 |

(*1) 3'-APH-producing bacterium;
(*2) 2'-AAD-producing bacterium;
(*3) 3-AAC-producing bacterium;
(*4) 6'-AAC-producing bacterium
(*5) 2'-AAC-producing bacterium.

The antibacterial spectra of other examples of the novel compounds of this invention, i.e. 5-demethoxy-4-N-(N-formimidoylglycyl)-KA-6606 II ($R_1$=$CH_3$, $R_2$=H, $R_3$=—$COCH_2NHCH$=NH) [compound D], and 4-N-(N-amidinoglycyl)-5-demethoxy-KA-6606 II ($R_1$=$CH_3$, $R_2$=H, and

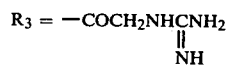

[compound No. E] are given in Table 2 in comparison with a 4-N-glycyl compound (5-de-O-methyl-KA-6606 I).

TABLE 2

| Test bacteria | Minimum inhibition concentration (mcg/ml) | | |
|---|---|---|---|
| | Control | D | E |
| Staphylococcus aureus 209P | 0.2 | 0.2 | 0.2 |
| Bacillus subtilis ATCC 6633 | 0.2 | ≦0.1 | ≦0.1 |
| Streptococcus faecalis | 12.5 | 12.5 | 12.5 |
| Escherichia coli NIHJ | 1.56 | 1.56 | 1.56 |
| Escherichia coli K-12 ML1410 | 3.13 | 1.56 | 1.56 |
| Escherichia coli K-12 ML1410 R-81 (*1) | 3.13 | 1.56 | 3.13 |
| Escherichia coli K-12 ML1410 R-82 (*2) | 3.13 | 3.13 | 3.13 |
| Escherichia coli K-12 ML1410 R-101 (*3) | 3.13 | 1.56 | 3.13 |
| Escherichia coli 176 (*4) | 1.56 | 0.78 | 0.78 |
| Proteus vulgaris OX-19 | 1.56 | 0.78 | 0.78 |
| Proteus inconstans (*5) | 1.56 | 1.56 | 1.56 |
| Klebsiela pneumoniae PCI602 | 1.56 | 0.78 | 1.56 |
| Pseudomonas aeruginosa No. 12 | 0.39 | 0.39 | 0.39 |
| Pseudomonas aeruginosa No. 99 (*6) | 50 | >100 | >100 |
| Pseudomonas aeruginosa A3 | 3.13 | 3.13 | 6.25 |
| Pseudomonas aeruginosa GN-315 (*7) | 3.13 | 6.25 | 12.5 |
| Pseudomonas aeruginosa PST-1 (*8) | 6.25 | 25 | 50 |
| Serratia marcescens | 0.78 | 0.78 | 0.78 |

(*1) 3'-APH-I;
(*2) 3'-APH-II;
(*3) 2'-AAD;
(*4) 3-AAC-II;
(*5) 2'-AAC;
(*6) 3-AAC-I;
(*7) 6'-AAC;
(*8) 3-AAC-III.

EXAMPLE 1

(a) One gram of a compound (5-de-O-methyl-KA-6606 II) of the following formula was dissolved in 10 ml of water.

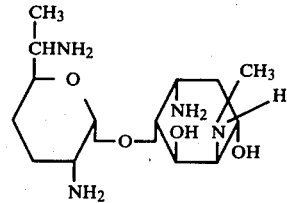

Anhydrous sodium carbonate (1.3 g) and 40 ml of methanol were added to the solution, and 2.6 ml of carbobenzoxy chloride was added dropwise with ice cooling. The mixture was stirred for 3 hours with ice cooling, and the reaction mixture was concentrated to dryness. After addition of chloroform, the residue was washed with water, and dried. The solvent was distilled off to give 2.6 g of colorless crystals. Recrystallization from benzene gave 1,4,2',6'-tetrakis-N-benzyloxycarbonyl-5-de-O-methyl-KA-6606 II as colorless needles having a melting point of 153° to 154° C.

Elemental analysis for $C_{46}H_{54}N_4O_{12}$:

| | C | H | N |
|---|---|---|---|
| Calculated (%): | 64.62 | 6.27 | 6.55 |

| | C | H | N |
|---|---|---|---|
| Found (%): | 64.49 | 6.33 | 6.61 |
| Specific rotation: | $[\alpha]_D^{23}$ + 44° (c 1, CHCl$_3$) | | |

(b) One hundred milligrams of the N-protected compound obtained in (a) was dissolved in 2 ml of dioxane, and 1.5 ml of a 0.1 M aqueous solution of barium hydroxide was added. The mixture was stirred at 60° C. for 1 hour. The reaction mixture was neutralized with dry ice, and the insoluble matter was removed by filtration. The filtrate was concentrated to dryness. The residue was separated by preparative thin-layer chromatography (chloroform-methanol=15:1) to give 68 mg of 1,2',6'-tris-N-benzyloxycarbonyl-3-0:4-N-carbonyl-5-de-O-methyl-KA-6606 II as a colorless solid.

Elemental analysis for C$_{39}$H$_{46}$N$_4$O$_{11}$: Calculated (%): C: 62.72; H: 6.21; N: 7.50; Found (%): C: 62.48; H: 6.10; N: 7.28.

Specific rotation: $[\alpha]_D^{23}$ +33° (c 1, CHCl$_3$).

IR ($\nu_{max}^{CHCl_3}$ cm$^{-1}$): 1760 (cyclic carbamate).

PMR ($\delta$ CDCl$_3$): 1.07 (3H, d, J=6 Hz, C—CH$_3$), 2.87 (3H, s, N—CH$_3$).

(c) 223 mg of the N,O-protected compound obtained in (b) above was dissolved in 5 ml of anhydrous dimethyl formamide, and 43 mg of 50% oil dispersion of sodium hydride was added with ice cooling. Then, 0.12 ml of N,N-dimethylsulfamoyl chloride was added, and the mixture was stirred for 1 hour with ice cooling. Acetic acid (0.4 ml) was added to the reaction mixture, and 50 ml of ice water was added. The precipitated solid was collected by filtration, washed with water and n-hexane, and dried. The resulting colorless powder was purified by preparative thin-layer chromatography (chloroform-methanol=20:1) to give 167 mg of 1,2',6'-tris-N-benzyloxycarbonyl-3-0:4-N-carbonyl-5-de-O-methyl-5-O-(N,N-dimethylsulfamoyl)-KA-6606 II as a colorless solid.

Elemental analysis for C$_{41}$H$_{52}$N$_5$O$_{13}$S:

| | C | H | N | S |
|---|---|---|---|---|
| Calculated (%): | 57.60 | 6.13 | 8.19 | 3.75 |
| Found (%): | 57.86 | 6.01 | 7.93 | 3.44 |
| Specific rotation: $[\alpha]_D^{23}$ + 35° (c 1, CHCl$_3$) | | | | |
| IR ($\nu_{max}^{CHCl_3}$ cm$^{-1}$): | 1765 (cyclic carbamate) | | | |
| | 1170 (sulfamoyl) | | | |
| PMR ($\delta$ CDCl$_3$): | 1.08 | (3H, d, J = 6.5Hz, C—CH$_3$) | | |
| | 2.84 | (6H, s, SO$_2$N(CH$_3$)$_2$) | | |
| | 2.92 | (3H, s, N—CH$_3$) | | |

(d) 135 mg of the 5-O-dimethylsulfamoyl compound obtained in (c) above was dissolved in 3 ml of acetic acid, and catalytically reduced at room temperature and atmospheric pressure using palladium black as a catalyst. The catalyst was removed from the reaction mixture by filtration, and the filtrate was concentrated to dryness. The residue was dissolved in 100 ml of water, and adsorbed to a column of CM-Sephadex C-25 (NH$_4$+ form) (5 ml). The column was washed with water, and eluted with 0.7 M aqueous ammonia. The eluate was concentrated to dryness. The residue was dissolved in 3 ml of liquid ammonia, and 100 mg of metallic sodium was added at −70° C. The mixture was stirred for 3 hours. Water was added to the reaction mixture to decompose sodium, and the mixture was concentrated to dryness. The residue was dissolved in 2 ml of water, and heated at 60° C. for 3 hours. The product was diluted to 100 ml with water. The diluted solution was neutralized with 4 N sulfuric acid, passed through a column of CM-Sephadex, and treated in a customary manner to give 15 mg of 5-demethoxy-KA-6606II of the following formula as a colorless solid.

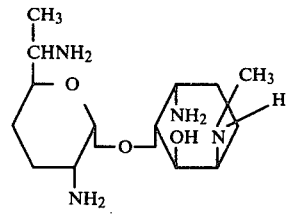

Elemental analysis for C$_{14}$H$_{30}$N$_4$O$_3$·H$_2$O:

| | C | H | N |
|---|---|---|---|
| Calculated (%): | 52.48 | 10.07 | 17.49 |
| Found (%): | 52.31 | 9.83 | 17.24 |

Specific rotation: $[\alpha]_D^{22}$ + 119° (c 1, H$_2$O)
PMR [$\delta$ D$_2$O (TMS external standard)]
  1.51 (3H, d, J = 7Hz, C—CH$_3$)
  2.80 (3H, s, N—CH$_3$)
  5.44 (1H, d, J = 3.7Hz, anomeric H)
  1.7–2.4 (8H, m, C—CH$_2$—C)

EXAMPLE 2

(a) 30 mg of 5-demethoxy-KA-6606II (Example 1, d) was dissolved in 1 ml of methanol, and 75 mg of nickel acetate tetrahydrate was added. The mixture was stirred for 30 minutes, and then 80 mg of benzyloxycarbonyloxysuccinimide was added. The mixture was stirred at room temperature for 3 hours. To the reaction mixture was added 1 ml of conc. aqueous ammonia, and the mixture was stirred for 1 hour and concentrated to dryness. To the residue were added 10 ml of chloroform and 10 ml of 4 N aqueous ammonia. The chloroform layer was separated, washed with 4 N aqueous ammonia and dried, followed by distilling off the solvent. The residue was dissolved in 2.3 ml of dioxane, and 0.15 ml of triethylamine and 80 mg of an N-hydroxysuccinimide ester of N-benzyloxycarbonylglycine was added. The mixture was heated overnight at 60° C. The reaction mixture was concentrated, and the residue was separated and purified by preparative thin-layer chromatography (silica gel; chloroform-methanol=13:1) to give 61 mg of tetrakis-N-benzyloxycarbonyl-5-demethoxy-KA-6606 I, as a colorless solid.

Elemental analysis for C$_{48}$H$_{57}$N$_5$O$_{12}$:

| | C | H | N |
|---|---|---|---|
| Calculated (%): | 64.34 | 6.41 | 7.82 |
| Found (%): | 64.51 | 6.43 | 7.56 |

Specific rotation: $[\alpha]_D^{23}$ + 38° (c 2, CHCl$_3$)
IR ($\nu_{max}^{CHCl_3}$ cm$^{-1}$):  1635 (amide 1)
PMR ($\delta$ CDCl$_3$):  1.08  (3H, d, J = 6.5Hz, C—CH$_3$)
  2.88  (3H, s, N—CH$_3$).

(b) 60 mg of the resulting N-protected compound was dissolved in 1 ml of acetic acid, and catalytically reduced using palladium black as a catalyst. After the reaction, the catalyst was removed by filtration. The filtrate was diluted with 160 ml of water, and neutralized with aqueous ammonia. The solution was passed through a column of CM-Sephadex C-25 (NH$_4$+ form)

(12 ml) to cause adsorption of the desired substance. The column was washed with water and then eluted with aqueous ammonia having a concentration ranging from 0.05 N to 0.5 N by a concentration gradient method. On lyophilizing fractions containing the desired substance, 21 mg of 5-demethoxy-KA-6606 I of the following formula was obtained as a colorless solid.

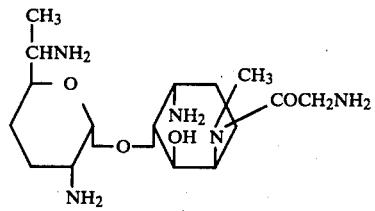

Elemental analysis for $C_{16}H_{33}N_5O_4 \cdot H_2O$:

| | C | H | N |
|---|---|---|---|
| Calculated (%): | 50.91 | 9.35 | 18.55 |
| Found (%): | 50.68 | 9.21 | 18.23 |

Specific rotation: $[\alpha]_D^{22}$ + 118° (c 1, $H_2O$)
PMR ($\delta D_2O$): 
  1.51 (3H, d, J = 6.5Hz, c—CH₃)
  1.8–2.4 (8H, m, C—CH₂—C)
  3.45 (3H, s, N—CH₃)
  3.99 (2H, s, N—C(=O)—CH₂—NH₂)
  5.45 (1H, d, J = 4Hz, anomeric H).

EXAMPLE 3

(a) The same reaction and treatment as in Example 1, (a) were performed using 300 mg of a compound of the following formula (5-de-O-methyl-KA-6606 VI).

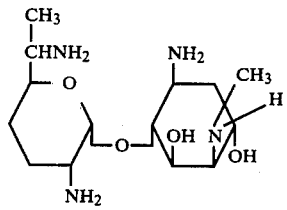

There was obtained 760 mg of tetrakis-N-benzyloxycarbonyl-5-de-O-methyl-KA 6606 VI as a colorless solid.

Elemental analysis for $C_{46}H_{54}N_4O_{12}$:

| | C | H | N |
|---|---|---|---|
| Calculated (%): | 64.62 | 6.37 | 6.55 |
| Found (%): | 64.90 | 6.18 | 6.48 |

Specific rotation: $[\alpha]_D^{22}$ + 51° (c 1, $CHCl_3$)
PMR ($\delta$ $CDCl_3$): 
  1.16 (3H, d, J = 6Hz, C—CH₃)
  2.89 (3H, s, N—CH₃)
  7.3–7.4 (20H, m, 4 × $C_6H_5$)

(b) Using 540 mg of the above N-protected compound, the same operation as in Example 1, (b) was performed. Purification by silica gel chromatography (chloroformmethanol=20:1) gave 384 mg of 1,2',6'-tris-N-benzyloxycarbonyl-3-0:4-N-carbonyl-5-de-O-methyl-KA-6606 VI as a colorless solid.

Elemental analysis for $C_{39}H_{46}N_4O_{11}$:

| | C | H | N |
|---|---|---|---|
| Calculated (%): | 62.72 | 6.21 | 7.50 |
| Found (%): | 62.70 | 5.90 | 7.34 |

Specific rotation: $[\alpha]_D^{22}$ + 48° (c 1, $CHCl_3$)
IR ($\nu_{max}^{CHCl_3}$ cm⁻¹): 1760 (cyclic carbamate)
PMR ($\delta$ $CDCl_2$): 
  1.15 (3H, d, J = 6Hz, C—CH₃)
  2.87 (3H, s, N—CH₃)

(c) Using 318 mg of the N,O-protected compound obtained above, the same operation as in Example 1, (c) was performed. There was obtained 275 mg of 1,2',6'-tris-N-benzyloxycarbonyl-3-0:4-N-carbonyl-5-de-O-methyl-5-O-(N,N-dimethylsulfamoyl)-KA-6606 VI as a colorless solid.

Elemental analysis for $C_{41}H_{52}N_5O_{13}S$:

| | C | H | N | S |
|---|---|---|---|---|
| Calculated (%): | 57.60 | 6.13 | 8.19 | 3.75 |
| Found (%): | 57.51 | 5.87 | 7.98 | 3.63 |

Specific rotation: $[\alpha]_D^{22}$ + 39° (c 1, $CHCl_3$)
IR ($\nu_{max}^{CHCl_3}$ cm⁻¹): 1760 cyclic carbonate, 1170 [$SO_2N(CH_3)_2$]
PMR ($\delta$ $CDCl_3$): 
  1.17 (3H, d, J = 6Hz, C—CH₃)
  2.85 [6H, s, $SO_2N(CH_3)_2$]
  2.89 (3H, s, N—CH₃)

(d) Using 260 mg of the above 5-O-dimethylsulfamoyl compound, the same operation as in Example 1, (d) was performed. Purification by ion-exchange chromatography on CM-Sephadex C-25 ($NH_4^+$ form) gave 38 mg of 5-demethoxy-KA-6606 VI of the following formula as a colorless solid.

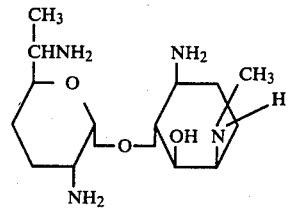

Elemental analysis for $C_{14}H_{30}N_4O_3 \cdot 1/2H_2CO_3 \cdot H_2O$:

| | C | H | N |
|---|---|---|---|
| Calculated (%): | 49.55 | 9.46 | 15.94 |
| Found (%): | 49.25 | 9.18 | 15.81 |

Specific rotation: $[\alpha]_D^{22}$ + 72° (c 1, $H_2O$)
PMR [$\delta$ $CDCl_3$ (TMS external standard)]:
  1.53 (3H, d, J = 6.5Hz, C—CH₃)
  2.86 (3H, s, N—CH₃)
  5.52 (1H, d, J = 3.5Hz, anomeric H)
  1.7–2.4 (8H, m, $CCH_2$—C)

EXAMPLE 4

(2) Using 26 mg of 5-demethoxy-KA-6606 VI (Example 3, (d)), the same operation as in Example 2, (a) was performed. There was obtained 58 mg of 1,2',6'-tris-N-benzyloxycarbonyl-4-N-(N'-benzyloxycarbonylglycyl)-5-demethoxy-KA-6606 VI as a colorless solid.

Elemental analysis for $C_{48}H_{57}N_5O_{12}$:

| | C | H | N |
|---|---|---|---|
| Calculated (%): | 64.34 | 6.41 | 7.82 |
| Found (%): | 64.21 | 6.19 | 7.62 |

-continued

| | | |
|---|---|---|
| Specific rotation: $[\alpha]_D^{22} + 28°$ (c 1, CHCl₃) | | |
| IR ($\nu_{max}^{CHCl_3}$ cm⁻¹): | 1640 (amide I) | |
| PMR ($\delta$ CDCl₃): | 1.19 | (3H, d, J = 6Hz, C—CH₃) |
| | 2.90 | (3H, s, N—CH₃) |

(b) Using 48 mg of the N-protected compound, the same operation as in Example 2, (b) was performed. There was obtained 14 mg of 5-demethoxy-4-N-glycyl-KA-6606 VI of the following formula as a colorless solid.

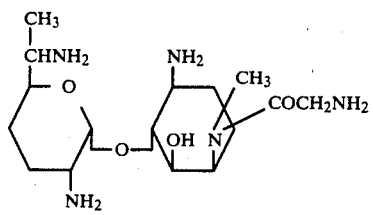

Elemental analysis for $C_{16}H_{33}N_5O_4 \cdot 3/2H_2O$:

| | C | H | N |
|---|---|---|---|
| Calculated (%): | 49.72 | 9.39 | 18.12 |
| Found (%): | 49.97 | 9.08 | 18.03 |
| Specific rotation: $[\alpha]_D^{22} + 108°$ (c 1, H₂O) | | | |
| PMR [$\delta$ D₂O (TMS external standard)]: | | | |
| 1.53 (3H, d, J = 6.5 Hz, C—CH₃) | | | |
| 3.58 (3H, s, N—CH₃) | | | |
| 4.01 (2H, s, CO—CH₂—NH₂) | | | |
| 5.40 (1H, d, J = 3.3 Hz, anomeric H) | | | |

EXAMPLE 5

(a) Using 330 mg of a compound of the following formula (5-de-O-methyl-KA-7038 III), the same operation as in Example 1, (a) was performed.

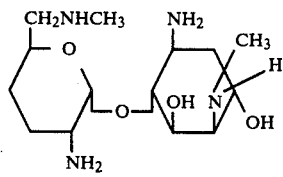

There was obtained 820 mg of tetrakis-N-benzyloxycarbonyl-5-de-O-methyl-KA-7038 III as a colorless solid.
Elementjal analysis for $C_{46}H_{54}N_4O_{12}$:

| | C | H | N |
|---|---|---|---|
| Calculated (%): | 64.62 | 6.37 | 6.55 |
| Found (%): | 64.59 | 6.21 | 6.38 |
| Specific rotation: $[\alpha]_D^{22} + 62°$ (c 1, CHCl₃) | | | |
| PMR ($\delta$ CDCl₃): 2.89 (3H, s, N—CH₃) | | | |
| 2.92 (3H, s, N—CH₃) | | | |

(b) Using 795 mg of the above N-protected compound, the same operation as in Example 1, (b) was performed. There was obtained 503 mg of 1,2′,6′-tris-N-benzyloxycarbonyl-3-0:4-N-carbonyl-5-de-O-methyl-KA-7038 III as a colorless solid.
Elemental analysis for $C_{39}H_{46}N_4O_{11}$:

| | C | H | N |
|---|---|---|---|
| Calculated (%): | 62.72 | 6.21 | 7.50 |
| Found (%): | 62.45 | 6.02 | 7.28 |
| Specific rotation: $[\alpha]_D^{22} + 46°$ (c 1, CHCl₃) | | | |
| IR ($\nu_{max}^{CHCl_3}$ cm⁻¹): 1760 (cyclic carbamate) | | | |
| PMR ($\delta$ CDCl₃): 2.81 (3H, s, N—CH₃) | | | |
| 2.90 (3H, s, N—CH₃) | | | |

(c) When the same operation as in Example 1, (c) was performed using 480 mg of the above N,O-protected compound, 411 mg of 1,2′,6′-tris-N-benzyloxycarbonyl-3-0:4-N-carbonyl-5-de-O-methyl-5-O-(N,N-dimethylsulfamoyl)-KA-7038 III was obtained as a colorless solid.

Elemental analysis for $C_{41}H_{52}N_5O_{13}S$:

| | C | H | N | S |
|---|---|---|---|---|
| Calculated (%): | 57.60 | 6.13 | 8.19 | 3.75 |
| Found (%): | 57.50 | 5.88 | 7.86 | 3.71 |
| Specific rotation: $[\alpha]_D^{22} + 41°$ (c 1, CHCl₃) | | | | |
| IR ($\nu_{max}^{CHCl_3}$ cm⁻¹): 1760 (cyclic carbamate) | | | | |
| 1170 (sulfamoyl) | | | | |
| PMR ($\delta$ CDCl₃): 2.82 (3H, s, N—CH₃) | | | | |
| 2.91 (3H, s, N—CH₃) | | | | |

(d) When the same operation as in Example 1, (d) was performed using 300 mg of the above 5-O-sulfamoyl compound, 31 mg of 5-demethoxy-KA-7038 III of the following formula was obtained as a colorless solid.

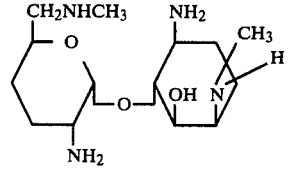

Elemental analysis for $C_{14}H_{30}N_4O_3 \cdot H_2O$:

| | C | H | N |
|---|---|---|---|
| Calculated (%): | 52.48 | 10.07 | 17.49 |
| Found (%): | 52.24 | 9.99 | 17.23 |
| Specific rotation: $[\alpha]_D^{22} + 36°$ (c 1, H₂O) | | | |
| PMR [$\delta$ D₂O (TMS external standard)]: | | | |
| 2.80 (3H, s, N—CH₃) | | | |
| 2.83 (3H, s, N—CH₃) | | | |
| 5.54 (1H, d, J = 3.3 Hz, anomeric H) | | | |

EXAMPLE 6

(a) When the same operation as in Example 2 (a) was performed using 26 mg of 5-demetoxy-KA-7038 III (Example 5, (d)), 46 mg of 1,2′,6′-tris-N-benzyloxycarbonyl-4-N-(N′-benzyloxycarbonylglycyl)-5-demethoxy-KA-7038 III (i.e., tetrakis-N-benzyloxycarbonyl-5-demethoxy-KA-7038 I) as a colorless solid.
Elemental analysis for $C_{48}H_{57}N_5O_{12}$:

| | C | H | N |
|---|---|---|---|
| Calculated (%): | 64.34 | 6.41 | 7.82 |
| Found (%): | 64.08 | 6.20 | 7.96 |
| Specific rotation: $[\alpha]_D^{22} + 32°$ (c 1, CHCl₃) | | | |
| PMR ($\delta$ CDCl₃): 2.91 (6H, s, N—CH₃) | | | |

(b) When the same operation as in Example 2 (b) was performed using 40 mg of the above N-protected compound, 12 mg of 5-demethoxy-KA-7038 I of the following formula was obtained as a colorless solid.

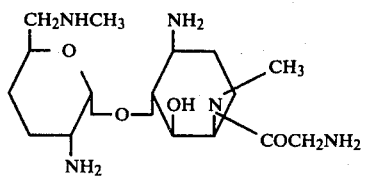

Elemental analysis for $C_{16}H_{33}N_5O_4 \cdot H_2CO_3$:

| | C | H | N |
|---|---|---|---|
| Calculated (%): | 48.44 | 8.37 | 16.62 |
| Found (%): | 48.21 | 8.02 | 16.74 |
| Specific rotation: $[\alpha]_D^{22} + 112°$ (c 1, $H_2O$) | | | |
| PMR [δ $D_2O$ (TMS external standard)]: | | | |
| 2.84 (3H, s, 6'-N—$CH_3$) | | | |
| 3.61 (3H, s, 4-N—$CH_3$) | | | |
| 5.40 (1H, d, J = 3 Hz, anomeric H) | | | |

EXAMPLE 7

(a) Two grams of 1,2',6'-tris-N-benzyloxycarbonyl-3-0:4-N-carbonyl-5-de-O-methyl-KA-6606 II (Example 1 (b)) was dissolved in 40 ml of dichloromethane, and at −10° C., 4 ml of pyridine and 1.6 ml of sulfuryl chloride were added. The mixture was allowed to stand at −10° C. for 12 hours, and then at 5° C. for 4 hours. The reaction mixture was poured into a mixture of 200 ml of chloroform and 200 ml of a saturated aqueous solution of sodium hydrogen carbonate. The chloroform layer was separated, washed with a saturated aqueous solution of sodium hydrogen carbonate, and dried, followed by distilling off the solvent. The residue was dissolved in 40 ml of benzene, and heated at 70° C. for 3 hours, and the solvent was distilled off. The residue was chromatographed on a silica gel column using chloroform-methanol (100:1) as an eluent to give 1.3 g of 1,2',6'-tris-N-benzyloxycarbonyl-3-0:4-N-carbonyl-5-chloro-5-demethoxy-KA-6606 II as a colorless solid.

Elemental analysis for $C_{39}H_{45}ClN_4O_{10}$:

| | C | H | N | Cl |
|---|---|---|---|---|
| Calculated (%): | 61.21 | 5.93 | 7.32 | 4.63 |
| Found (%): | 60.98 | 5.81 | 7.51 | 4.55 |
| Specific rotation: $[\alpha]_D^{23} + 24°$ (c 2, $CHCl_3$) | | | | |
| IR ($\nu_{max}^{CHCl_3}$ cm$^{-1}$): 1760 (cyclic carbamate) | | | | |
| PMR (δ $CDCl_3$): 1.06 (3H, d, J = 6 Hz, C—$CH_3$) | | | | |
| 2.86 (3H, s, N—$CH_3$) | | | | |

(b) 1.2 g of the above 5-chloro compound was dissolved in 24 ml of toluene, and 1.5 ml of tri-n-butyl stannane was added. After purging with nitrogen, 20 mg of azobisisobutyronitrile was added. The mixture was heated at 80° C. for 4 hours. The reaction mixture was concentrated to dryness. The residue was chromatographed on a silica gel column using chloroform-methanol (100:1) as an eluent to give 1.13 g of 1,2',6'-tris-N-benzyloxycarbonyl-3-0:4-N-carbonyl-5-demethoxy-KA-6606 II as a colorless solid.

Elemental analysis for $C_{39}H_{46}N_4O_{10}$:

| | C | H | N |
|---|---|---|---|
| Calculated (%): | 64.10 | 6.34 | 7.67 |
| Found (%): | 63.95 | 6.32 | 7.61 |
| Specific rotation: $[\alpha]_D^{24} + 3°$ (c 2, $CHCl_3$) | | | |
| IR ($\nu_{max}^{CHCl_3}$ cm$^{-1}$): 1755 (cyclic carbamate) | | | |
| PMR [δ $CDCl_3$]: 1.07 (3H, d, J = 7 Hz, C—$CH_3$) | | | |
| 2.73 (3H, s, N—$CH_3$) | | | |

(c) 1.1 g of the 5-demethoxy compound was dissolved in 20 ml of dioxane, and 25 ml of a 0.3 M aqueous solution of barium hydroxide was added. The mixture was stirred overnight at 60° C. The reaction mixture was neutralized with carbon dioxide gas, and the insoluble matter was removed by filtration. The filtrate was concentrated to dryness. The residue was dissolved in 10 ml of acetonitrile, and 500 mg of N-benzyloxycarbonyl glycine and 500 mg of dicyclohexylcarbodiimide were added. The mixture was stirred at room temperature for 3 hours. The insoluble matter was removed by filtration, and the filtrate was concentrated to dryness. The residue was chromatographed on a silica gel column using chloroform-acetone (6:1) as an eluent to give 820 mg of tetrakis-N-benzyloxycarbonyl-5-demethoxy-KA-6606 I as a colorless solid. This compound was identical with the standard product obtained in Example 2 (a) in specific rotation, IR spectrum and PMR spectrum.

(d) In the same way as in Example 2 (b), 5-demethoxy-KA-6606 I was obtained from the above N-protected compound.

EXAMPLE 8

(a) 600 mg of 1,2',6'-tris-N-benzyloxycarbonyl-3-0:4-N-carbonyl-5-de-O-methyl-KA-6606 II (Example 1, (b)) was dissolved in 10 ml of pyridine, and 750 mg of tosyl chloride was added. The mixture was stirred overnight at 50° C. After adding a small amount of methanol to the reaction mixture, the solvent was distilled off, and the residue was dissolved in 20 ml of chloroform. The solution was washed with an aqueous solution of sodium hydrogen carbonate and then with water, and dried to distilled off the solvent. The residue was chromatographed on a column of silica gel using chloroform-ethyl acetate (7:2) as an eluent. Fractions containing the desired product were treated with in a customary manner to give 670 mg of 1,2',6'-tris-N-benzyloxycarbonyl-3-0:4-N-carbonyl-5-de-O-methyl-5-O-tosyl-KA-6606 II as a colorless solid.

Elemental analysis for $C_{46}H_{52}N_4O_{13}S$:

| | C | H | N | S |
|---|---|---|---|---|
| Calculated (%): | 61.32 | 5.82 | 6.22 | 3.56 |
| Found (%): | 61.05 | 5.50 | 6.11 | 3.28 |
| Specific rotation: $[\alpha]_D^{23} + 37°$ (c 1, $CHCl_3$) | | | | |
| IR ($\nu_{max}^{CHCl_3}$ cm$^{-1}$): 1770 (carbamate) | | | | |
| 1180 ($OSO_2$) | | | | |
| PMR [δ $CDCl_3$ ppm]: 1.08 (3H, d, J = 6.5 Hz, 6'-C—$CH_3$) | | | | |

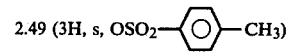

2.49 (3H, s, $OSO_2$—⟨○⟩—$CH_3$)

2.69 (3H, s, N—$CH_3$)

(b) 670 mg of the above tosyl compound was dissolved in 8.4 ml of a 10% acetonitrile solution of tetrabutyl ammonium fluoride, and the solution was heated at 80° C. for 8 hours. Chloroform (40 ml) was added to the reaction mixture, and the mixture was washed with water, and dried, followed by distilling off the solvent. The residue was chromatographed on a column of silica gel using chloroform-ethyl acetate (5:2) as an eluent. Fractions containing the desired product were treated in a customary manner to give 324 mg of 1,2',6'-tris-N-benzyloxycarbonyl-3-0:4-N-carbonyl-5-demethoxy-5-eno-KA-6606 II as a colorless solid.

Elemental analysis for $C_{39}H_{44}N_4O_{10}$:

|  | C | H | N |
|---|---|---|---|
| Calculated (%): | 64.27 | 6.09 | 7.69 |
| Found (%): | 64.55 | 6.33 | 7.41 |
| Specific rotation: | $[\alpha]_D^{24} - 34°$ (c 1, CHCl$_3$) | | |
| IR ($\nu_{max}^{CHCl_3}$ cm$^{-1}$): | 1760 (carbamate) | | |
| PMR ($\delta$ CDCl$_3$ ppm): | 1.10 (3H, d, J = 6.5 Hz, C—CH$_3$) | | |
|  | 2.82 (3H, s, N—CH$_3$) | | |
|  | 5.91 (2H, s, olefinic H) | | |

(c) 117 mg of the above N-protected compound was dissolved in 1 ml of acetic acid, and 2 ml of 25% hydrogen bromide-acetic acid was added. The mixture was left to stand at room temperature for 2 hours. To the reaction mixture was added 30 ml of n-hexane, and the resulting precipitate was collected by filtration. It was dissolved in 3 ml of 0.5 N barium hydroxide, and the solution was heated at 80° C. for 1 hour. The reaction mixture was neutralized with sulfuric acid, and diluted with 100 ml of water. The resulting precipitate was removed by filtration. The filtrate was charged onto a column of CM-Sephadex C-25 (NH$_4^+$ form) column, and developed with aqueous ammonia having a concentration ranging from 0.1 N to 0.5 N by the concentration gradient method. Fractions containing the desired product were lyophilized to give 14 mg of 5-demethoxy-5-eno-KA-6606 II of the following formula as a colorless powder.

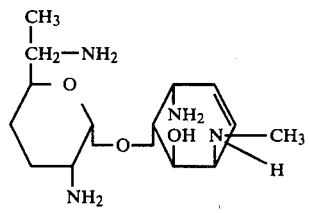

Elemental analysis for $C_{14}H_{28}N_4O_3 \cdot H_2O$:

|  | C | H | N |
|---|---|---|---|
| Calculated (%): | 52.81 | 9.50 | 17.60 |
| Found (%): | 52.48 | 9.15 | 17.36 |
| Specific rotation: | $[\alpha]_D^{24} - 14°$ (c 0.5, H$_2$O) | | |

PMR [$\delta$ D$_2$O ppm (TMS external standard)]:

| 1.53 | (3H, d, J = 6.5Hz, C—CH$_3$) |
| 2.88 | (3H, s, N—CH$_3$) |
| 5.52 | (1H, d, J = 4.0Hz, H-1') |
| 6.24 | (2H, s, olefinic H) |

EXAMPLE 9

(a) 60 mg of 5-demethoxy-5-eno-KA-6606 II (Example 9, (c)) was dissolved in 2 ml of methanol, and 150 mg of nickel acetate tetrahydrate was added. The mixture was stirred for 30 minutes and 160 mg of benzyloxycarbonyloxysuccinimide was added. The mixture was stirred for 3 hours, and 1 ml of conc. aqueous ammonia was added. The mixture was stirred for 30 minutes, and the solvent was distilled off. The residue was dissolved in 20 ml of chloroform, washed with 3 N aqueous ammonia and water, and dried, followed by distilling off the solvent.

The residue was dissolved in 4 ml of dioxane, and 150 mg of N-hydroxysuccinimide ester of N-benzyloxycarbonylglycine and 0.2 ml of triethylamine were added. The mixture was heated overnight at 60° C. After the reaction, the solvent was distilled off, and the residue was chromatographed on a silica gel column using chloroform ethyl acetate (5:2) as an eluent. Fractions containing the desired product were treated in a customary manner to give 81 mg of tetrakis-N-benzyloxycarbonyl-5-demethoxy-5-eno-KA-6606 I as a colorless solid.

Elemental analysis for $C_{48}H_{55}N_5O_{12}$:

|  | C | H | N |
|---|---|---|---|
| Calculated (%): | 64.49 | 6.20 | 7.83 |
| Found (%): | 64.22 | 6.01 | 7.56 |
| Specific rotation: | $[\alpha]_D^{23} - 21°$ (c 1, CHCl$_3$) | | |
| IR ($\nu_{max}^{CHCl_3}$ cm$^{-1}$): | 1630 (amide I) | | |
| PMR ($\delta$ CDCl$_3$ ppm): | 1.07 (3H, d, J = 6.5Hz, C—CH$_3$) | | |
|  | 2.89 (3H, s, N—CH$_3$) | | |

(b) When the same operation as in Example 2 (b) was performed using 81 mg of the above N-protected compound, 10 mg of 5-demethoxy-5-eno-KA-6606 I of the following formula was obtained as colorless powder.

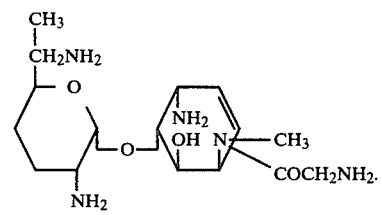

Elemental analysis values for $C_{16}H_{31}N_5O_4 \cdot H_2O$:

|  | C | H | N |
|---|---|---|---|
| Calculated (%): | 51.18 | 8.86 | 18.65 |
| Found (%): | 50.91 | 8.53 | 18.36 |
| Specific rotation: | $[\alpha]_D^{23} + 8.0°$ (c 0.5, H$_2$O) | | |

PMR [$\delta$ D$_2$O ppm (TMS external standard)]:

| 1.56 | (3H, d, J = 6.5Hz, C—CH$_3$) |
| 3.52 | (3H, s, N—CH$_3$) |
| 5.58 | (1H, d, J = 3.4Hz, anomeric H) |

EXAMPLE 10

(a) 1.14 g of 1,2',6'-tris-N-benzyloxycarbonyl-3-0:4-N-carbonyl-5-demethoxy-KA-6606 II obtained in Example 7 (b) was dissolved in 17 ml of dioxane, and 17 ml of a 0.45 M aqueous solution of barium hydroxide was added. The mixture was heated at 60° C. for 16 hours with stirring. The reaction mixture was neutralized with carbon dioxide gas, and the insoluble matter was removed by filtration. The filtrate was concentrated to dryness. The residue was dissolved in chloroform, washed with water and dried, followed by distilling off the solvent.

The residue was dissolved in 25 ml of dioxane, and 750 mg of N-hydroxysuccinimide ester of N-diphenylphosphinothioylglycine and 0.8 ml of triethylamine were added. The mixture was left to stand overnight at room temperature. The reaction mixture was concentrated to dryness, and the residue was dissolved in chloroform, washed with water, and dried, followed by distilling off the solvent. The residue was chromatographed on a silica gel column using chloroform-ethyl acetate (5:2) as an eluent and treated in a customary manner to give 643 mg of 1,2',6'-tris-N-benzyloxycarbonyl-5-demethoxy-4-N-(N-diphenylphosphinothioyl-glycyl)-KA-6606 II as a colorless solid.

Elemental analysis for $C_{52}H_{60}N_5O_{10}PS$:

|  | C | H | N | P | S |
|---|---|---|---|---|---|
| Calculated (%): | 63.85 | 6.18 | 7.16 | 3.17 | 3.28 |
| Found (%): | 63.99 | 6.35 | 7.41 | 2.98 | 3.11 |
| Specific rotation: | $[\alpha]_D^{25} + 53°$ (c 0.5, CHCl$_3$) | | | | |
| IR ($\nu_{max}^{CHCl_3}$ cm$^{-1}$): | 1640 | (amide I) | | | |
| PMR ($\delta$ CDCl$_3$ ppm): | 1.08 | (3H, d, J = 7.0Hz, C—CH$_3$) | | | |
|  | 2.81 | (3H, s, N—CH$_3$) | | | |
|  | 7.3–7.4 | (25H, m, aromatic H) | | | |

(b) 520 mg of the resulting 4-N-protected glycyl compound was dissolved in 15 ml of a mixture of tetrahydrofuran and conc. hydrochloric acid (5:1), and the solution was left to stand at room temperature for 24 hours. The reaction mixture was adjusted to pH 5 with aqueous ammonia. The tetrahydrofuran was distilled off, and 15 ml of water was added. The mixture was extracted with chloroform. The extract was washed with a 0.5 N aqueous solution of sodium hydroxide and water, and dried, followed by distilling off the solvent. The residue was chromatographed on a silica gel column using chloroform-methanol-conc. aqueous ammonia (60:10:1) as an eluent, and treated in a customary manner to give 190 mg of 1,2',6'-tris-N-benzyloxycarbonyl-5-demethoxy-KA-6606 I as a colorless solid.

Elemental analysis for $C_{40}H_{51}N_5O_{10}$:

|  | C | H | N |
|---|---|---|---|
| Calculated (%): | 63.06 | 6.75 | 9.19 |
| Found (%): | 62.77 | 6.89 | 9.45 |
| Specific rotation: | $[\alpha]_D^{25} + 71°$ (c 1, CHCl$_3$) | | |
| IR ($\nu_{max}^{CHCl_3}$ cm$^{-1}$): | 1625 | (amide I) | |
| PMR ($\delta$ CDCl$_3$ ppm): | 1.09 | (3H, d, J = 7.0Hz, C—CH$_3$) | |
|  | 2.89 | (3H, s, N—CH$_3$) | |
|  | 7.3 | (15 H, m, aromatic H). | |

(c) 190 mg of the resulting 4 N-glycyl compound was dissolved in 4 ml of anhydrous methanol, and 90 mg of ethylformimidate hydrochloride was added. A small amount of sodium methoxide was added to adjust the pH of the mixture to 7. Then, the mixture was allowed to stand overnight at room temperature. A small amount of acetic acid was added to the reaction mixture to adjust its pH to 5. It was concentrated to dryness. To the residue was added 25 ml of chloroform to leach out the product. The solvent was distilled off. The residue was chromatographed on a silica gel column using chloroform-methanol-acetic acid (6:2:1) as an eluent, and treated in a customary manner to give 146 mg of 1,2',6'-tris-N-benzyloxycarbonyl-5-demethoxy-4-N-(N-formimidoylglycyl)-KA-6606 II monoacetate as a colorless solid.

Elemental analysis for $C_{41}N_{52}N_6O_{10} \cdot CH_3CO_2H$:

|  | C | H | N |
|---|---|---|---|
| Calculated (%): | 60.84 | 6.65 | 9.90 |
| Found (%): | 60.58 | 6.82 | 9.71 |
| Specific roatation: | $[\alpha]_D^{25} + 52°$ (c 1, MeOH) | | |
| IR ($\nu_{max}^{CHCl_3}$ cm$^{-1}$): | 1630 | (amide I) | |
| PMR ($\delta$CDCl$_3$ ppm): | 1.06 | (3H, d, J = 7.0Hz, C—CH$_3$) | |
|  | 3.0 | (3H, s, N—CH$_3$) | |

(d) 146 mg of the formimidoylated N-protected compound was dissolved in 3 ml of acetic acid, and 80 mg of 5% palladium carbon was added. The above compound was thus catalytically reduced at room temperature. The reaction mixture was filtered and the filtrate was diluted with 300 ml of water and neutralized with aqueous ammonia. The neutralized filtrate was charged on a column of CM-Sephadex C-25 (NH$_4^+$ form), and developed with an aqueous solution of ammonium formate having a concentration ranging from 0.5 N to 2 N by the concentration gradient method. Fractions containing the desired product were collected and lyophilized to give a powder. The powder was dissolved in 2 ml of cold water, acidified to pH 2 with hydrochloric acid, and lyophilized to give 29 mg of 5-demethoxy-4-N-(N-formimidoylglycyl)-KA-6606 II tetrahydrochloride monohydrate as a colorless powder.

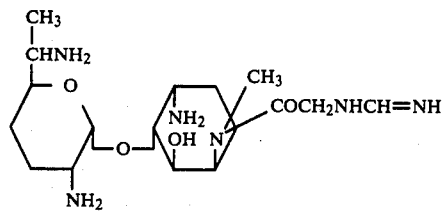

Elemental analysis for $C_{17}H_{34}N_6O_4 \cdot 4HCl \cdot H_2O$:

|  | C | H | N | Cl |
|---|---|---|---|---|
| Calculated (%): | 37.10 | 7.33 | 15.27 | 25.77 |
| Found (%): | 37.42 | 7.08 | 15.53 | 25.44 |
| Specific rotation: | $[\alpha]_D^{25} + 78°$ (c 1, H$_2$O0) | | | |
| IR ($\nu_{max}^{KBr}$ cm$^{-1}$): | 1705 | (formimidoyl) | | |
|  | 1620 | (amide I) | | |
| PMR ($\delta$ D$_2$O ppm): | 1.81 | (3H, d, J = 7.0Hz, C—CH$_3$) | | |
|  | 3.53 | (3H, s, N—CH$_3$) | | |
|  | 5.99 | (1H, d, J = 3.4Hz, anomeric H) | | |
|  | 8.46 | (1H, s, CH=NH) | | |

EXAMPLE 11

(a) 200 mg of 1,2',6'-tris-N-benzyloxycarbonyl-5-demethoxy-KA-6606 I obtained in Example 10 (b) was dissolved in 6.8 ml of methanol, and 137 mg of 1-nitroguanyl-3,5-dimethylpyrazole was added. The mixture was maintained at room temperature for 24 hours to perform the reaction. The reaction mixture was concentrated and extracted with chloroform. The extract was chromatographed on a silica gel column using chloroform-methanol (15:1) as an eluent, and treated in a customary manner to give 154 mg of 1,2',6'-tris-N-benzyloxycarbonyl-4-N-(N-nitroamidinoglycyl)-5-demethoxy-KA-6606 II.

Elemental analysis for $C_{41}H_{52}N_8O_{12}$:

|  | C | H | N |
|---|---|---|---|
| Calculated (%): | 58.01 | 6.17 | 13.20 |
| Found (%): | 58.22 | 6.15 | 12.95 |
| Specific rotation: | $[\alpha]_D^{22} + 71.0°$ (c 1, CHCl$_3$) | | |
| IR $\nu_{max}^{CHCl_3}$cm$^{-1}$): | 1680, 1595 | (guanidyl) | |
|  | 1540, 1302 | (N—No$_2$) | |

| -continued | | |
|---|---|---|
| PMR (δ CDCl$_3$ ppm): | 0.75 | (3H, C—CH$_3$) |
| | 3.00 | (3H, s, N—Ch$_3$) |

(b) 120 mg of the resulting nitroamidino compound was dissolved in 4 ml of acetic acid, and catalytically reduced at room temperature in the presence of 120 mg of 5% palladium carbon. The catalyst was removed by filtration, and the filtrate was diluted with cold water to a volume of 450 ml. The pH of the diluted filtrate was adjusted to 6 with conc. aqueous ammonia, and it was adsorbed on a column of CM-Sephadex C-25 (NH$_4$+ form). The column was washed with water and a 0.5 M aqueous solution of ammonium formate, and then eluted with a 1 M aqueous solution of ammonium formate. Fractions containing the desired product were lyophilized to give 78 mg of 4-N-(N-amidinoglycyl)-5-demethoxy-KA-6606 II formate.

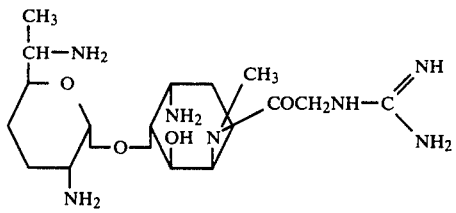

The corresponding hydrochloride produced from the above salt in a customary manner had the following properties.

Elemental analysis for C$_{17}$H$_{35}$N$_7$O$_4$.4HCl.H$_2$O:

| | C | H | N | Cl |
|---|---|---|---|---|
| Calculated (%): | 36.12 | 7.31 | 17.34 | 25.08 |
| Found (%): | 35.98 | 7.29 | 17.21 | 24.81 |
| Specific rotation: | [α]$_D^{24}$ + 68.0° (c 1, H$_2$O) | | | |
| IR (ν$_{max}^{KBr}$ cm$^{-1}$): | 1628 | (amide I, guanidium) | | |
| PMR (δ D$_2$O, ppm): | 1.84 | (3H, d, J = 6.5Hz, C—CH$_3$) | | |
| | 3.57 | (3H, s, N—CH$_3$) | | |
| | 4.82 | (2H, s, CO—CH$_2$—NH) | | |
| | 6.05 | (1H, d, J = 3.5Hz, 1'-H). | | |

What we claim is:

1. A compound of the formula:

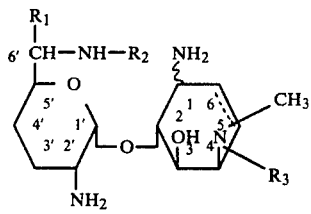

wherein R$_1$ and R$_2$ are different and each represents a hydrogen atom or a methyl group, R$_3$ represents a hydrogen atom, or a group represented by the formula —COCH$_2$NHR' in which R' is a member selected from the group consisting of a hydrogen atom, —CH═NH and $$-\underset{\underset{NH}{\parallel}}{C}NH_2,$$

and the symbol $\equiv\equiv\equiv$ between the carbon atoms at the 5- and 6-positions represents a single or double bond, or an acid addition salt thereof.

2. An antibiotic composition which comprises an antibiotically effective amount of a compound of the formula:

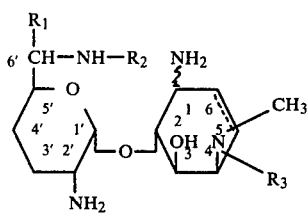

wherein R$_1$ and R$_2$ are different and each represents a hydrogen atom or a methyl group, R$_3$ represents a hydrogen atom, or a group represented by the formula —COCH$_2$NHR' in which R' is a member selected from the group consisting of a hydrogen atom, —CH═NH and $$-\underset{\underset{NH}{\parallel}}{C}NH_2,$$

and the symbol $\equiv\equiv\equiv$ between the carbon atoms at the 5- and 6-positions represents a single or double bond, and a pharmaceutically acceptable diluent or carrier.

3. A composition of claim 2 wherein the amount of the compound of the formula or its pharmaceutically acceptable acid addition salt is about 0.01 to about 99.5% by weight based on the weight of the composition.

* * * * *